United States Patent
Feld et al.

(10) Patent No.: US 11,583,424 B2
(45) Date of Patent: Feb. 21, 2023

(54) CONSTRAINING STRUCTURE WITH NON-LINEAR AXIAL STRUTS

(71) Applicant: TriReme Medical, LLC, Pleasanton, CA (US)

(72) Inventors: Tanhum Feld, Moshav Merhavya (IL); Eitan Konstantine, Orinda, CA (US)

(73) Assignee: TriReme Medical, LLC, Pleasanton, CA (US)

( * ) Notice: Subject to any disclaimer, the term of this patent is extended or adjusted under 35 U.S.C. 154(b) by 585 days.

(21) Appl. No.: 16/666,925

(22) Filed: Oct. 29, 2019

(65) Prior Publication Data

US 2020/0139093 A1 May 7, 2020

Related U.S. Application Data

(63) Continuation of application No. 14/936,458, filed on Nov. 9, 2015, now Pat. No. 10,524,825, which is a (Continued)

(51) Int. Cl.
*A61F 2/915* (2013.01)
*A61B 17/3207* (2006.01)
(Continued)

(52) U.S. Cl.
CPC ...... *A61F 2/915* (2013.01); *A61B 17/320725* (2013.01); *A61B 17/50* (2013.01);
(Continued)

(58) Field of Classification Search
CPC .. A61M 2025/1086; A61M 2025/1084; A61M 2025/1031; A61M 2025/1059;
(Continued)

(56) References Cited

U.S. PATENT DOCUMENTS 2,701,559 A 2/1955 Cooper
2,854,983 A 10/1958 Baskin
(Continued)

FOREIGN PATENT DOCUMENTS

CN 1568165 A 1/2005
EP 0 565 796 10/1993
(Continued)

OTHER PUBLICATIONS

AngioSculpt XL PT Scoring Balloon Catheter Brochure, AngioScore, Inc., Rev. C, May 2013.
(Continued)

*Primary Examiner* — Katherine H Schwiker
(74) *Attorney, Agent, or Firm* — Knobbe, Martens, Olson & Bear, LLP

(57) ABSTRACT

A constraining structure for use with a balloon catheter can include multiple longitudinal struts and multiple, sinusoidal shaped radial rings. The constraining structure can expand to form a pattern of channels including substantially square windows. The constraining structure can modify, restrict, and control a shape and/or size of the balloon when inflated. Inflating the balloon catheter within the constraining structure can provide nonuniform pressure on a vessel wall adjacent the balloon.

26 Claims, 2 Drawing Sheets

Related U.S. Application Data continuation of application No. 13/761,525, filed on Feb. 7, 2013, now Pat. No. 9,179,936.

(60) Provisional application No. 61/596,618, filed on Feb. 8, 2012.

(51) Int. Cl.

| | | |
|---|---|---|
| *A61M 25/10* | (2013.01) | |
| *A61B 17/50* | (2006.01) | |
| *A61M 29/02* | (2006.01) | |

(52) U.S. Cl.
CPC . *A61M 25/104* (2013.01); *A61F 2002/91558* (2013.01); *A61F 2002/91566* (2013.01); *A61M 29/02* (2013.01); *A61M 2025/1084* (2013.01)

(58) Field of Classification Search
CPC .... A61M 2025/1072; A61M 2025/109; A61M 2025/1095; A61M 2025/1097; A61M 25/104; A61B 17/320725; A61F 2/915; A61F 2002/91558; A61F 2002/91566
See application file for complete search history.

(56) References Cited

U.S. PATENT DOCUMENTS

| | | |
|---|---|---|
| 3,045,677 A | 7/1962 | Wallace |
| 3,467,101 A | 9/1969 | Fogarty et al. |
| 3,825,013 A | 7/1974 | Craven |
| 4,327,736 A | 5/1982 | Inoue |
| 4,456,011 A | 6/1984 | Warnecke |
| 4,483,340 A | 11/1984 | Fogarty et al. |
| 4,637,396 A | 1/1987 | Cook |
| 4,723,549 A | 2/1988 | Wholey et al. |
| 4,796,629 A | 1/1989 | Grayzel |
| 4,921,484 A | 5/1990 | Hillstead |
| 4,976,711 A | 12/1990 | Parins et al. |
| 4,998,539 A | 3/1991 | Delsanti |
| 5,071,407 A | 12/1991 | Porter et al. |
| 5,100,386 A | 3/1992 | Inoue |
| 5,133,732 A | 7/1992 | Wilkor |
| 5,176,693 A | 1/1993 | Pannek |
| 5,181,911 A | 1/1993 | Shturman |
| 5,190,058 A | 3/1993 | Jones et al. |
| 5,196,024 A | 3/1993 | Barath |
| 5,222,971 A | 6/1993 | Willard et al. |
| 5,224,945 A | 7/1993 | Pannek, Jr. |
| 5,263,963 A | 11/1993 | Garrison et al. |
| 5,308,356 A | 5/1994 | Blackshear, Jr. et al. |
| 5,320,634 A | 6/1994 | Vigil et al. |
| 5,336,178 A | 8/1994 | Kaplan |
| 5,336,234 A | 8/1994 | Vigil et al. |
| 5,344,419 A | 9/1994 | Spears |
| 5,449,372 A | 9/1995 | Schmaltz et al. |
| 5,456,666 A | 10/1995 | Campbell et al. |
| 5,456,667 A | 10/1995 | Ham et al. |
| 5,460,607 A | 10/1995 | Miyata et al. |
| 5,484,411 A | 1/1996 | Inderbitzen et al. |
| 5,501,694 A | 3/1996 | Ressemann et al. |
| 5,527,282 A | 6/1996 | Segal |
| 5,556,408 A | 9/1996 | Farhat |
| 5,562,620 A | 10/1996 | Klein et al. |
| 5,571,086 A | 11/1996 | Kaplan et al. |
| 5,607,442 A | 3/1997 | Fischell et al. |
| 5,609,574 A | 3/1997 | Kaplan et al. |
| 5,616,149 A | 4/1997 | Barath |
| 5,620,457 A | 4/1997 | Pinchasik et al. |
| 5,628,746 A | 5/1997 | Clayman |
| 5,628,755 A | 5/1997 | Heller et al. |
| 5,643,210 A | 7/1997 | Iacob |
| 5,643,312 A | 7/1997 | Fischell et al. |
| 5,695,469 A | 12/1997 | Segal |
| 5,702,410 A | 12/1997 | Klunder et al. |
| 5,713,863 A | 2/1998 | Vigil et al. |
| 5,730,698 A | 3/1998 | Fischell et al. |
| 5,733,303 A | 3/1998 | Israel et al. |
| 5,735,816 A | 4/1998 | Lieber et al. |
| 5,755,781 A | 5/1998 | Jayaraman |
| 5,772,681 A | 6/1998 | Leoni |
| 5,776,181 A | 7/1998 | Lee et al. |
| 5,797,935 A | 8/1998 | Barath |
| 5,810,767 A | 9/1998 | Klein |
| 5,827,321 A | 10/1998 | Roubin et al. |
| 5,863,284 A | 1/1999 | Klein |
| 5,868,708 A | 2/1999 | Hart et al. |
| 5,868,719 A | 2/1999 | Tsukernik |
| 5,868,779 A | 2/1999 | Ruiz |
| 5,868,783 A | 2/1999 | Tower |
| 5,869,284 A | 2/1999 | Cao et al. |
| 5,904,679 A | 5/1999 | Clayman |
| 5,906,639 A | 5/1999 | Rudnick et al. |
| 5,919,200 A | 7/1999 | Stambaugh et al. |
| 5,961,490 A | 10/1999 | Adams |
| 5,967,984 A | 10/1999 | Chu et al. |
| 5,987,661 A | 11/1999 | Peterson |
| 6,013,055 A | 1/2000 | Bampos et al. |
| 6,036,689 A | 3/2000 | Tu et al. |
| 6,036,708 A | 3/2000 | Sciver |
| 6,053,913 A | 4/2000 | Tu et al. |
| 6,059,810 A | 5/2000 | Brown et al. |
| 6,059,811 A | 5/2000 | Pinchasik et al. |
| 6,077,298 A | 6/2000 | Tu et al. |
| 6,102,904 A | 8/2000 | Vigil et al. |
| 6,106,548 A | 8/2000 | Roubin et al. |
| 6,129,706 A | 10/2000 | Janacek |
| 6,156,265 A | 12/2000 | Sugimoto |
| 6,190,403 B1 | 2/2001 | Fischell et al. |
| 6,206,910 B1 | 3/2001 | Berry et al. |
| 6,217,608 B1 | 4/2001 | Penn et al. |
| 6,235,043 B1 | 5/2001 | Reiley et al. |
| 6,241,762 B1 | 6/2001 | Shanley |
| 6,245,040 B1 | 6/2001 | Inderbitzen et al. |
| 6,258,099 B1 | 7/2001 | Mareiro et al. |
| 6,261,319 B1 | 7/2001 | Kveen et al. |
| 6,309,414 B1 | 10/2001 | Rolando et al. |
| 6,319,251 B1 | 11/2001 | Tu et al. |
| 6,334,871 B1 | 1/2002 | Dor et al. |
| 6,361,545 B1 | 3/2002 | Macoviak et al. |
| 6,416,539 B1 | 7/2002 | Hassdenteufel |
| 6,454,775 B1 | 9/2002 | Demarais et al. |
| 6,540,722 B1 | 4/2003 | Boyle et al. |
| 6,605,107 B1 | 8/2003 | Klein |
| 6,616,678 B2 | 9/2003 | Nishtala et al. |
| 6,626,861 B1 | 9/2003 | Hart et al. |
| 6,652,548 B2 | 11/2003 | Evans et al. |
| 6,656,351 B2 | 12/2003 | Boyle |
| 6,695,813 B1 | 2/2004 | Boyle et al. |
| 6,702,834 B1 | 3/2004 | Boylan et al. |
| 6,939,320 B2 | 9/2005 | Lennox |
| 6,942,680 B2 | 9/2005 | Grayzel et al. |
| 7,156,869 B1 | 1/2007 | Pacetti |
| 7,186,237 B2 | 3/2007 | Meyer et al. |
| 7,357,813 B2 | 4/2008 | Burgermeister |
| 7,686,824 B2 | 3/2010 | Konstantino et al. |
| 7,691,119 B2 | 4/2010 | Farnan |
| 7,708,748 B2 | 5/2010 | Weisenburgh, II et al. |
| 7,753,907 B2 | 7/2010 | DiMatteo et al. |
| 7,803,149 B2 | 9/2010 | Bates et al. |
| 7,931,663 B2 | 4/2011 | Farnan et al. |
| 8,172,793 B2 | 5/2012 | Bates et al. |
| 8,257,305 B2 | 9/2012 | Speck et al. |
| 8,348,987 B2 | 1/2013 | Eaton |
| 8,388,573 B1 | 3/2013 | Cox |
| 8,439,868 B2 | 5/2013 | Speck et al. |
| 9,179,936 B2 | 11/2015 | Feld et al. |
| 9,199,066 B2 | 12/2015 | Konstantino et al. |
| 9,216,033 B2 | 12/2015 | Feld et al. |
| 9,375,328 B2 | 6/2016 | Farnan |
| 9,415,140 B2 | 8/2016 | Speck |
| 9,649,476 B2 | 5/2017 | Speck et al. |
| 10,220,193 B2 | 3/2019 | Feld et al. |
| 10,232,148 B2 | 3/2019 | Konstantino et al. |
| 10,524,825 B2 | 1/2020 | Feld et al. |

(56) References Cited

U.S. PATENT DOCUMENTS

| | | |
|---|---|---|
| 10,549,077 B2 | 2/2020 | Konstantino et al. |
| 11,000,680 B2 | 5/2021 | Konstantino et al. |
| 11,234,843 B2 | 2/2022 | Feld et al. |
| 2002/0010489 A1 | 1/2002 | Grayzel et al. |
| 2003/0023200 A1 | 1/2003 | Barbut et al. |
| 2003/0040790 A1 | 2/2003 | Furst |
| 2003/0065354 A1 | 4/2003 | Boyle |
| 2003/0078606 A1 | 4/2003 | Lafontaine et al. |
| 2003/0114915 A1 | 6/2003 | Mareiro et al. |
| 2003/0114921 A1 | 6/2003 | Yoon |
| 2003/0120303 A1 | 6/2003 | Boyle et al. |
| 2003/0144726 A1 | 7/2003 | Majercak et al. |
| 2003/0153870 A1 | 8/2003 | Meyer et al. |
| 2003/0195609 A1 | 10/2003 | Berenstein et al. |
| 2003/0212449 A1 | 11/2003 | Cox |
| 2004/0034384 A1 | 2/2004 | Fukaya |
| 2004/0073284 A1 | 4/2004 | Bates et al. |
| 2004/0111108 A1* | 6/2004 | Farnan ............... A61M 25/104 623/1.16 |
| 2004/0143287 A1 | 7/2004 | Konstantino et al. |
| 2004/0210235 A1 | 10/2004 | Deshmukh |
| 2004/0210299 A1 | 10/2004 | Rogers et al. |
| 2004/0230293 A1 | 11/2004 | Yip et al. |
| 2005/0021071 A1 | 1/2005 | Konstantino et al. |
| 2005/0021130 A1 | 1/2005 | Kveen et al. |
| 2005/0049677 A1 | 3/2005 | Farnan |
| 2005/0125053 A1 | 6/2005 | Yachia et al. |
| 2005/0271844 A1 | 12/2005 | Mapes et al. |
| 2006/0008606 A1 | 1/2006 | Horn et al. |
| 2006/0015133 A1 | 1/2006 | Grayzel et al. |
| 2006/0085025 A1 | 4/2006 | Farnan et al. |
| 2006/0085058 A1 | 4/2006 | Rosenthal et al. |
| 2006/0149308 A1 | 7/2006 | Melsheimer et al. |
| 2006/0259005 A1 | 11/2006 | Konstantino et al. |
| 2006/0271093 A1* | 11/2006 | Holman ............... A61M 25/10 606/194 |
| 2007/0073376 A1 | 3/2007 | Krolik et al. |
| 2007/0173923 A1 | 7/2007 | Savage et al. |
| 2008/0255508 A1 | 10/2008 | Wang |
| 2009/0036964 A1 | 2/2009 | Heringes et al. |
| 2009/0038752 A1 | 2/2009 | Weng et al. |
| 2009/0105686 A1 | 4/2009 | Snow et al. |
| 2009/0192453 A1 | 7/2009 | Wesselman |
| 2009/0227949 A1 | 9/2009 | Knapp et al. |
| 2009/0240270 A1 | 9/2009 | Schneider et al. |
| 2009/0319023 A1 | 12/2009 | Hildebrand et al. |
| 2010/0042121 A1 | 2/2010 | Schnieder et al. |
| 2010/0234875 A1 | 9/2010 | Allex et al. |
| 2010/0241215 A1 | 9/2010 | Hansen et al. |
| 2010/0331809 A1 | 12/2010 | Sandhu et al. |
| 2011/0066225 A1 | 3/2011 | Trollsas et al. |
| 2011/0071616 A1 | 3/2011 | Clarke et al. |
| 2011/0152905 A1* | 6/2011 | Eaton ............... A61M 25/104 606/159 |
| 2011/0172698 A1 | 7/2011 | Davies et al. |
| 2012/0059401 A1 | 3/2012 | Konstantino et al. |
| 2012/0083733 A1 | 4/2012 | Chappa |
| 2012/0245607 A1 | 9/2012 | Gershony et al. |
| 2013/0046237 A1 | 2/2013 | Speck et al. |
| 2013/0116655 A1 | 5/2013 | Bacino et al. |
| 2013/0190725 A1 | 7/2013 | Pacetti et al. |
| 2013/0211381 A1 | 8/2013 | Feld |
| 2014/0276406 A1 | 9/2014 | Campbell et al. |
| 2015/0209556 A1 | 7/2015 | Timothy |
| 2016/0100964 A1 | 4/2016 | Feld et al. |
| 2019/0151627 A1 | 5/2019 | Konstantino et al. |
| 2019/0151631 A1 | 5/2019 | Feld et al. |
| 2020/0215311 A1 | 7/2020 | Konstantino et al. |
| 2021/0128891 A1 | 5/2021 | Konstantino et al. |
| 2021/0402160 A1 | 12/2021 | Konstantino et al. |
| 2022/0168120 A1 | 6/2022 | Feld et al. |

FOREIGN PATENT DOCUMENTS

| | | |
|---|---|---|
| EP | 0 623 315 | 11/1994 |
| EP | 0 832 608 | 4/1998 |
| EP | 1 042 997 | 10/2000 |
| EP | 2 035 291 | 3/2009 |
| JP | 2005-508709 | 4/2005 |
| JP | 2014-528809 | 10/2014 |
| WO | WO 98/05377 | 2/1998 |
| WO | WO 98/50101 | 11/1998 |
| WO | WO 00/57815 | 10/2000 |
| WO | WO 2002/068011 | 9/2002 |
| WO | WO 2003/041760 | 5/2003 |
| WO | WO 2005/020855 | 3/2005 |
| WO | WO 2011/112863 | 9/2011 |
| WO | WO 2013/066566 | 5/2013 |
| WO | WO 2013/114201 | 8/2013 |
| WO | WO 2013/119735 | 8/2013 |

OTHER PUBLICATIONS

Bearing Works, (PTFE) Polytetrafluoroethylene material specifications sheet, available online Feb. 11, 2018 at https://www.bearingworks.com/uploaded-assets/pdfs/retainers/ptfe-datasheet.pdf; printed Feb. 21, 2018, in 2 pages.

Brydson, J.A., "Plastics Materials—Sixth Edition," 1995, p. 510, available in part online from https://books.google.com/books?id=wmohBQAAQBAJ&lpg=PA510&ots=G_4Q-OMpB4&dq=young's%20modulus%20of%20PEBAx&pg=PA510#v=onepage&q=young's%20modulus%20of%20PEBAx&f=false; printed on May 5, 2017.

Kadish, A., et al. "Mapping of Atrial Activation With a Noncontact, Multielectrode Catheter in Dogs," *Circulation: Journal of the American Heart Association*, (Apr. 1999) 99: 1906-1913.

International Search Report for Appl. No. PCT/US13/25032, dated Apr. 19, 2013 in 8 pages.

"Materials Data Book," Cambridge University Engineering Department, 2003, pp. 1-41.

* cited by examiner

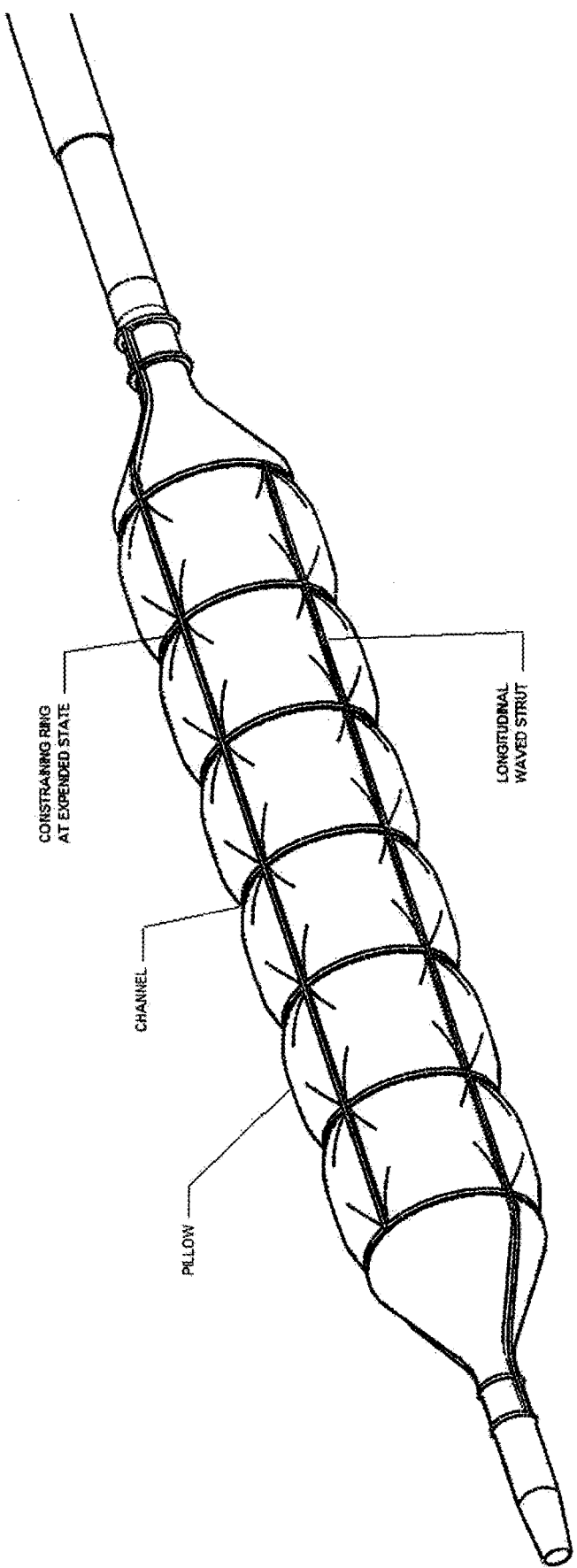

CONSTRAINING STRUCTURE WITH NON-LINEAR AXIAL STRUTS

This application is a continuation of U.S. patent application Ser. No. 14/936,458, filed Nov. 9, 2015, which is a continuation of U.S. patent application Ser. No. 13/761,525, filed Feb. 7, 2013, which claims the benefit of U.S. Provisional Application No. 61/596,618, filed Feb. 8, 2012, the entirety of which is incorporated by reference herein.

BACKGROUND OF THE INVENTION

Field of the Invention

The present invention is a balloon catheter for angioplasty procedures, comprising an elastic constraining structure mounted over the balloon where the structure has a mechanism of expansion to control the balloon inflation.

Conventional angioplasty balloons expand in an artery lesion at the least resistant areas of the lesion causing "dog bone" effect at the lesion ends and overexpansion in the softer areas, resulting in trauma to the vessel wall. Conventional angioplasty is associated with vessel displacement and its main mechanism of action is plaque compression where the vessel is significantly displaced or "pushed out" before reaction force can be generated and plaque compression takes place. During this process the balloon may expand in the axial direction (in addition to radial), a phenomenon that accelerates propagation of "cracks" in the vessel wall (dissections). This elongation continues after the balloon engages the lesion and the vessel wall and cause longitudinal stretch This mechanism of action causes a high rate of failure due to the vessel trauma (randomize studies in legs arteries document up to 40% acute failure rate and poor long term results with 20%-40% patency in one year). Attempts to modify the mechanism of action were mainly aimed at increasing the local force by adding cutting blades, wires or scoring elements that can penetrate into the vessel wall and create pre defined dissection plans. Those devices are used when encountering resistant lesions otherwise hard to crack open with conventional balloons. None of those technologies was designed to provide an alternative mechanism that leads to a gentler dilatation by minimizing vessel displacement and reducing the radial forces during balloon dilatation.

SUMMARY OF THE INVENTION

According to the present invention, a device that modifies the properties of an angioplasty balloon in order to provide uniform inflation and extraction of longitudinal forces in order to facilitate plaque extrusion and minimize vessel trauma. In the device presented herein, a novel constraining structure prevents non-cylindrical expansion using constraining rings that are spaced apart along the balloon working length leading to creation of small balloon segments (pillows) separates by grooves that facilitate plaque extrusion. The constraining structure also prevents longitudinal elongation of the balloon since it has a structure that shortens during expansion and constrains the balloon in both longitudinal and radial directions.

Computer simulation shows a decrease in radial forces using a balloon with the constraining structure. The constraining structure causes reduction in the rate of vessel dissections and perforations thru formation of an array of balloon pillows that provide gentle contact with the vessel wall and thru the formation of channels between these pillows that allow plaque flow and strain relief areas in the vessel wall.

Conventional balloon angioplasty does not provide strain relief to the vessel wall and suffer from high rate of dissections.

Other devices, such as cutting balloons and scoring devices (for example U.S. Pat. No. 7,691,119 Farnan) made to address resistant lesions by adding elements that can cut or score into the vessel wall and significantly, increase the local force ("focus force angioplasty"), but do not provide strain relief and gentle contact with the vessel wall. On the contrary, these devices include aggressive metallic components that are made to break hard plaque and mark their metal footprint on the vessel wall.

The constraining structure of the present invention takes advantage of the fact that by forcing the balloon into pillows topography the excessive length of the balloon is directed into a three dimensional shape and the surface area of the balloon increases. This mechanism shortens the overall balloon length during inflation and minimized longitudinal vessel stretch. Other devices such as stents or scoring cages that have structures over a balloon are using the balloon as an "activator" or expandable shell designed to increase the diameter of the stent or scoring stent and allow the balloon to inflate in full both radially and longitudinally and are therefore designed to expand as big as the inflated balloon, while the design present herein is made smaller than the inflated balloon, specifically aimed to modify, restrict and control the balloon inflated shape and size.

The combination of the advantages of the device described herein result in controlled non aggressive and predictable lesion dilation that addresses a major health concern.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows a scheme of the inflated device with circumferential and longitudinal pattern of channels and pillows.

DETAILED DESCRIPTION OF THE PREFERRED EMBODIMENT

Figure 1:
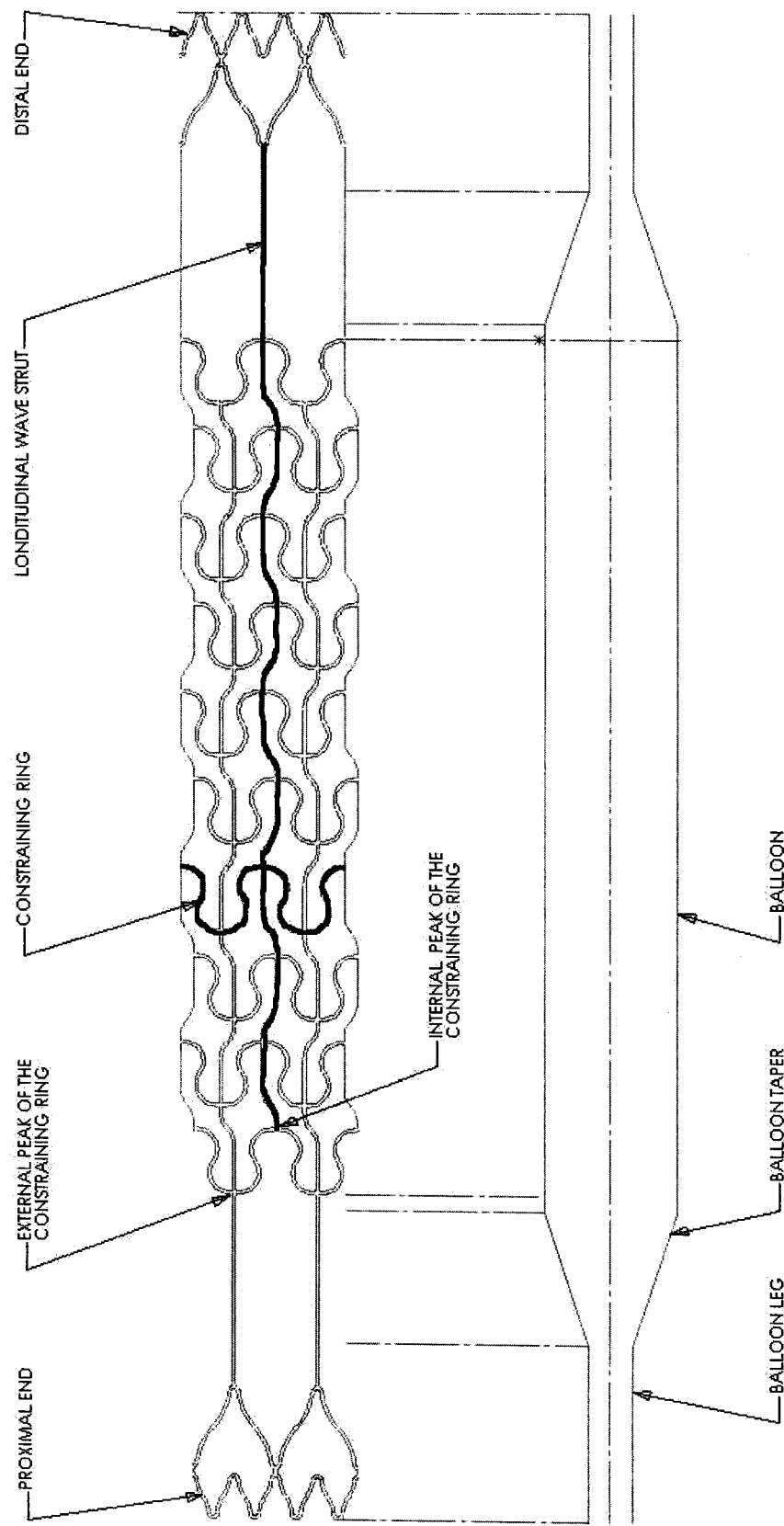
FIG. 1 show the layout of the constraining structure design adjacent to the balloon scheme, where the distal and proximal ends of the constraining structure are placed over the balloon legs, the constraining rings are spaced apart along the balloon length over the working length of the balloon, and an array of longitudinal waved struts interconnect between the constraining rings and the ends.

A balloon catheter comprising a catheter shaft and an inflatable balloon at its distal end and an elastic constraining structure is mounted over the balloon. The constraining structure is made from an elastic material such as Nitinol, elastic polymers or high strength fibers or mesh.

The device natural configuration is collapsed. Unlike "self-expending stents" it is not "self-expending" but to the contrary "self-closing": prior to expansion the constraining structure is tightly closed on the folded balloon. When the balloon is inflated the constraining structure is expanded by the balloon force up to a diameter smaller than the free inflated diameter of the balloon. The structure will self compressed back to a small diameter when the balloon is deflated. Typically the distal end and a proximal end of the constraining structure are fixedly attached to the catheter at both sides of the balloon to prevent it from disengaging with the catheter. Attachment is made by means of adhesive or thermal bonding or other method known in the art.

The constraining structure comprises an array of sinusoidal constraining rings spaced apart along the balloon working length. Each ring has a sinus curve length defined by the length of the ring when fully straitened. For each ring the sinus curve length is smaller than the balloon expanded circumference. When expanded the rings expand to its maximal expansion resulting in a substantially circular ring shape that is smaller in diameter than the balloon diameter and force a substantially circular channel around the balloon outer surface.

Expansion of the constraining rings results in an array of channels along the balloon length and also results in shortening of the balloon. It is easier to understand the shortening caused by the rings as it is obvious that if the rings were removed from an inflated balloon the balloon would elongate.

The maximum expanded diameter of the constraining structure is mainly controlled by the length of the sinus curve rings. The maximum expanded diameter could be 0.15 mm-0.3 mm smaller than the balloon free inflated diameter but it could also be in the range of 0.1 mm to 0.5 mm or exceed this range depending on the material of choice and the specifics of the design. For example for 3 mm balloon the maximum expanded diameter of the structure made of nitinol is in the range of 2.6 mm-2.85 mm. If the maximum expanded diameter is out of the desirable range the device will fail to perform. For example, if the maximum expanded diameter is similar or larger than the balloon free expanded diameter, the constraining structure would not be able to restrict the free expansion of the balloon and pillows will not form. If the structure is too small, the forces applied by the balloon would cause the structure to break and the device will fail, risking patient's safety.

The constraining rings are interconnected by a circumferential array of interlacing longitudinal waved struts. The number of struts is usually twice the number of the sine waves in the constraining ring. For example the structure scheme shows a two waves sine ring and therefore four longitudinal waved struts. Each strut begins near one end of the constraining structure and ends at the last constraining ring near the opposite end. It does not continue all the way to the opposite end in order to allow proper functionality and expansion. The following strut begins near the opposite end of the constraining structure and ends at the last constraining rings near the first end of the balloon, such that the opposing ends are not interconnected by the longitudinal waved struts.

This construction result in the last ring being connected to the ends with half the number of struts only. If the struts were to continue all the way to the opposing end it would restrict the first ring from expanding homogeneously over the balloon as the intermediate rings expand.

The struts connect to the first constraining rings at the external peaks of the ring and thus forming a structure that shortens when expanded. If the struts were connected to the first constraining rings at the internal peaks of the ring than the structure would elongate when expanded.

It is particularly important not to have "spine" or struts that are connected to both proximal and distal end of the balloon. The current structure in FIG. 1 in which two (or more) longitudinal struts are connected to the distal end of the balloon and two (or more) other interlacing struts connected to the proximal end of the balloon create "push/pull" forces during inflation and longitudinal struts are moving in opposing directions during inflation in order to apply compressive forces on the balloon and allow it to shorten. This "tilt" function supports expansion of the pillows at lower pressure. The longitudinal waved struts form longitudinal channels over the balloon outer surface and together with the circular channels formed by the rings it results in substantially square pattern of channels ("windows") and balloon pillows protruding in the windows.

What is claimed is:

1. A balloon catheter comprising:
   a catheter shaft;
   an inflatable balloon positioned at a distal portion of the catheter shaft; and
   a constraining structure mounted over the balloon and fixedly attached to the catheter shaft, the constraining structure comprising a plurality of struts, wherein each of the plurality of struts does not extend an entire length of the balloon,
   wherein the balloon catheter is configured to transition between a collapsed configuration and an expanded configuration,
   wherein in the expanded configuration, the plurality of struts form longitudinal channels in an outer surface of the inflatable balloon.

2. The balloon catheter of claim 1, wherein the balloon catheter is biased to the collapsed configuration.

3. The balloon catheter of claim 1, wherein in the collapsed configuration, the constraining structure is closed on the inflatable balloon.

4. The balloon catheter of claim 1, wherein in the collapsed configuration, the inflatable balloon is folded.

5. The balloon catheter of claim 1, wherein the constraining structure comprises nitinol.

6. The balloon catheter of claim 1, wherein the constraining structure comprises an elastic polymer.

7. The balloon catheter of claim 1, wherein the constraining structure comprises fibers.

8. The balloon catheter of claim 1, wherein the constraining structure comprises mesh.

9. The balloon catheter of claim 1, wherein each of the plurality of struts is only connected to one of a proximal end and a distal end of the constraining structure.

10. The balloon catheter of claim 1, wherein the plurality of struts are interconnected by a plurality of constraining rings.

11. The balloon catheter of claim 10, wherein in the expanded configuration, the plurality of constraining rings form circular channels in an outer surface of the inflatable balloon.

12. The balloon catheter of claim 1, wherein when expanded, the constraining structure is configured to apply compressive forces on the inflatable balloon.

13. The balloon catheter of claim 1, wherein the constraining structure is configured to prevent longitudinal elongation of the inflatable balloon.

14. The balloon catheter of claim 1, wherein the constraining structure is configured to shorten when expanded by the inflatable balloon.

15. The balloon catheter of claim 1, wherein the constraining structure is configured to constrain the inflatable balloon in both longitudinal and radial directions.

16. A balloon catheter comprising:
- a catheter shaft;
- an inflatable balloon positioned at a distal portion of the catheter shaft; and
- a constraining structure mounted over the balloon and fixedly attached to the catheter shaft, the constraining structure comprises nitinol, the constraining structure comprising a plurality of struts, wherein each of the plurality of struts does not extend an entire length of the balloon, wherein the balloon catheter is configured to transition between a collapsed configuration and an expanded configuration.

17. The balloon catheter of claim 16, wherein the balloon catheter is biased to the collapsed configuration.

18. The balloon catheter of claim 16, wherein in the collapsed configuration, the constraining structure is closed on the inflatable balloon.

19. The balloon catheter of claim 16, wherein in the collapsed configuration, the inflatable balloon is folded.

20. The balloon catheter of claim 16, wherein each of the plurality of struts is only connected to one of a proximal end and a distal end of the constraining structure.

21. The balloon catheter of claim 16, wherein the plurality of struts are interconnected by a plurality of constraining rings.

22. The balloon catheter of claim 21, wherein in the expanded configuration, the plurality of constraining rings form circular channels in an outer surface of the inflatable balloon.

23. The balloon catheter of claim 16, wherein when expanded, the constraining structure is configured to apply compressive forces on the inflatable balloon.

24. The balloon catheter of claim 16, wherein the constraining structure is configured to prevent longitudinal elongation of the inflatable balloon.

25. The balloon catheter of claim 16, wherein the constraining structure is configured to shorten when expanded by the inflatable balloon.

26. The balloon catheter of claim 16, wherein the constraining structure is configured to constrain the inflatable balloon in both longitudinal and radial directions.

* * * * *

UNITED STATES PATENT AND TRADEMARK OFFICE
CERTIFICATE OF CORRECTION

PATENT NO. : 11,583,424 B2
APPLICATION NO. : 16/666925
DATED : February 21, 2023
INVENTOR(S) : Tanhum Feld It is certified that error appears in the above-identified patent and that said Letters Patent is hereby corrected as shown below:

On the Title Page

Column 1 (Inventors), Line 2, delete "Eitan Konstantine," and insert -- Eitan Konstantino, --.

Signed and Sealed this
First Day of August, 2023

Katherine Kelly Vidal
Director of the United States Patent and Trademark Office